United States Patent
Convert et al.

(10) Patent No.: US 12,129,579 B2
(45) Date of Patent: Oct. 29, 2024

(54) METHOD FOR PRODUCING A TUBULAR COMPRESSION ITEM, AND ITEM THEREBY OBTAINED

(71) Applicant: THUASNE, Levallois Perret (FR)

(72) Inventors: Reynald Convert, Saint Martin la Plaine (FR); Aurélia Ruer, Saint Maurice en Gourgois (FR); Gérard Cattiaux, La Fouillouse (FR); Pascal Motet, Saint Etienne (FR)

(73) Assignee: THUASNE, Levallois Perret (FR)

( * ) Notice: Subject to any disclaimer, the term of this patent is extended or adjusted under 35 U.S.C. 154(b) by 0 days.

(21) Appl. No.: 17/408,784

(22) Filed: Aug. 23, 2021

(65) Prior Publication Data
US 2021/0395931 A1 Dec. 23, 2021

Related U.S. Application Data

(62) Division of application No. 14/426,793, filed as application No. PCT/FR2013/052039 on Sep. 4, 2013, now Pat. No. 11,131,044.

(30) Foreign Application Priority Data

Sep. 19, 2012 (FR) ...................................... 12 58771

(51) Int. Cl.
*D04B 1/26* (2006.01)
*A61F 13/08* (2006.01)
(Continued)

(52) U.S. Cl.
CPC .............. *D04B 1/265* (2013.01); *A61F 13/08* (2013.01); *D04B 1/106* (2013.01); *D04B 1/18* (2013.01); *D04B 15/18* (2013.01)

(58) Field of Classification Search
CPC ........... A61F 13/08; D04B 1/106; D04B 1/18; D04B 1/26; D04B 1/265
See application file for complete search history.

(56) References Cited

U.S. PATENT DOCUMENTS

| 1,577,752 A | * | 3/1926 | Price | .................. D04B 1/26 |
| | | | | 66/172 R |
| 1,795,131 A | * | 3/1931 | Lawson | .................. D04B 1/26 |
| | | | | 66/190 |

(Continued)

FOREIGN PATENT DOCUMENTS

| AT | 206576 | * 12/1959 |
| EP | 0003498 A2 | 8/1979 |

(Continued)

*Primary Examiner* — Megan E Lynch
(74) *Attorney, Agent, or Firm* — MH2 Technology Law Group, LLP (57) ABSTRACT

A tubular compression item having at least one leg part, one foot tip, one heel, one foot and one ribbed edge in the extension of the leg part delimiting an opening for introducing a foot into the item, is provided. The leg part has a height extending from the foot part up to the ribbed edge, and the leg part, the foot and the ribbed edge of the tubular compression item each comprise at least one knitting yarn. An elastic weft yarn is inserted between the stitches on the outer face and the stitches on the inner face of the leg part. The elastic weft yarn is inserted on at least 90% of the columns of stitches without forming any tuck stitch or loop stitch. The elastic weft yarn is maintained between two consecutive rows of stitches in the leg part. The foot tip and the heel each comprise at least one knitting yarn.

20 Claims, 8 Drawing Sheets

(51) Int. Cl.
*D04B 1/10* (2006.01)
*D04B 1/18* (2006.01)
*D04B 15/18* (2006.01)

(56) References Cited

U.S. PATENT DOCUMENTS

| | | | | |
|---|---|---|---|---|
| 2,054,059 | A * | 9/1936 | Longtin | D04B 1/106 66/190 |
| 2,188,241 | A * | 1/1940 | Davis | D04B 1/26 66/190 |
| 2,223,749 | A * | 12/1940 | Thurston | D04B 1/106 66/190 |
| 3,015,943 | A * | 1/1962 | Loizillon | D04B 1/26 66/202 |
| 3,301,018 | A * | 1/1967 | Knohl | D04B 9/46 66/190 |
| 3,402,575 | A | 9/1968 | Peberdy | |
| 3,935,718 | A * | 2/1976 | Carminati | D04B 9/46 66/14 |
| 3,946,577 | A * | 3/1976 | Townsend | D04B 9/10 66/14 |
| 3,995,322 | A * | 12/1976 | Chesebro, Jr. | D04B 1/26 66/172 E |
| 4,015,448 | A | 4/1977 | Knohl | |
| 4,109,492 | A * | 8/1978 | Roberts | D04B 9/54 66/172 E |
| 4,125,001 | A * | 11/1978 | Bryars | D04B 1/04 66/196 |
| 4,172,370 | A * | 10/1979 | Safrit | D04B 1/26 66/93 |
| 4,172,456 | A * | 10/1979 | Zens | D04B 1/265 66/178 A |
| 4,237,707 | A * | 12/1980 | Safrit | D04B 1/04 66/185 |
| 4,422,307 | A * | 12/1983 | Thorneburg | A41B 11/02 66/172 E |
| 4,499,742 | A * | 2/1985 | Burn | D04B 1/106 66/172 E |
| 4,502,301 | A * | 3/1985 | Swallow | A61F 13/08 66/178 A |
| 4,520,635 | A * | 6/1985 | Shields | A41B 11/02 66/185 |
| 4,561,267 | A * | 12/1985 | Wilkinson | D04B 1/26 66/178 A |
| 4,674,489 | A | 6/1987 | Lundy | |
| 4,732,015 | A * | 3/1988 | Abrams | D04B 15/61 66/185 |
| 4,958,507 | A * | 9/1990 | Allaire | D04B 9/54 66/185 |
| 5,540,063 | A * | 7/1996 | Ferrell | D04B 1/26 66/178 R |
| 6,151,922 | A * | 11/2000 | Shimasaki | D04B 1/02 66/61 |
| 6,158,253 | A * | 12/2000 | Svoboda | D04B 1/106 66/178 R |
| 6,216,495 | B1 * | 4/2001 | Couzan | A61F 13/08 66/178 R |
| 2002/0029012 | A1 * | 3/2002 | Gardon-Mollard | D04B 9/52 602/62 |
| 2006/0021390 | A1 | 2/2006 | Gebel et al. | |
| 2006/0085894 | A1 * | 4/2006 | Yakopson | D04B 1/265 2/69 |
| 2007/0029308 | A1 | 2/2007 | Arabeyre et al. | |
| 2007/0033711 | A1 * | 2/2007 | Achtelstetter | A41B 11/00 2/239 |
| 2007/0113593 | A1 * | 5/2007 | Jeong | D04B 1/02 66/180 |
| 2008/0249454 | A1 * | 10/2008 | Mills | D04B 1/265 602/63 |
| 2010/0137776 | A1 * | 6/2010 | Virkus | A61F 13/08 602/76 |
| 2012/0035510 | A1 * | 2/2012 | Cros | D04B 1/265 600/592 |
| 2012/0078156 | A1 * | 3/2012 | Platz | A61F 13/08 602/76 |
| 2012/0116282 | A1 * | 5/2012 | Cros | D04B 1/16 602/76 |
| 2013/0047313 | A1 * | 2/2013 | Windisch | D04B 1/28 2/69 |
| 2013/0263629 | A1 * | 10/2013 | Gaither | D04B 1/265 66/185 |
| 2015/0245951 | A1 * | 9/2015 | Convert | A61F 13/08 66/107 |

FOREIGN PATENT DOCUMENTS

| | | | | |
|---|---|---|---|---|
| EP | 0045287 | A1 | 2/1982 | |
| EP | 1621164 | A1 | 2/2006 | |
| EP | 1878822 | A1 | 1/2008 | |
| FR | 1428069 | * | 2/1966 | D04B 1/02 |
| FR | 1450226 | A | 5/1966 | |
| FR | 2181324 | A5 | 11/1973 | |
| FR | 2255406 | A1 | 7/1975 | |
| FR | 2781816 | A1 | 2/2000 | |
| FR | 2852509 | A1 | 9/2004 | |
| FR | 2888855 | A1 | 1/2007 | |
| GB | 479120 | * | 1/1938 | A61F 13/08 |
| GB | 786637 | * | 11/1957 | |
| GB | 898983 | * | 6/1962 | |
| GB | 951610 | * | 3/1964 | D04B 1/18 |
| SU | 108059 | A1 | 11/1956 | |
| WO | WO-2011143489 | A2 * | 11/2011 | A61F 13/08 |
| WO | 2012/101618 | A1 | 8/2012 | |

* cited by examiner

METHOD FOR PRODUCING A TUBULAR COMPRESSION ITEM, AND ITEM THEREBY OBTAINED

CROSS REFERENCE TO RELATED APPLICATIONS

This application is a divisional application of U.S. patent application Ser. No. 14/426,793, filed Mar. 9, 2015, now allowed, which is a § 371 of PCT/FR2013/052039 filed 4 Sep. 2013, which claims the benefit of priority of French Patent Application No. 12 58771 filed 19 Sep. 2012, the entire contents of which are herein incorporated by reference in their entireties.

BACKGROUND OF THE INVENTION

The present invention relates to the technical field of methods for manufacturing tubular compression items, in particular items exerting gradual compression from the ankle up to the top of the leg.

Compression items, socks or knee-length stockings, stockings, pantyhoses or further sleeves, are used for preventing or caring for venous circulation problems notably at the lower or upper limb, as well as pathologies related to malfunctions of the lymphatic system and reduction of edemas. Venous disorders may have several origins, among which are notably found: rigidification of the vein wall, alteration of the valvulae or further an increase in the diameter of the veins.

The local pressure exerted on a limb by an item with a compressive effect notably depends on the force-elongation characteristics of said item.

The pressure exerted on a limb is calculated by the following Laplace law:

$$P[\text{Pa or mmHg}] = (T[N] \times n)/(L[m] \times R[m]).$$

P represents the pressure exerted on a given point of the relevant limb.

L is the width of the relevant area of the limb and n represents the number of layers of the item with a compressive effect, positioned on said area.

T is the tension, expressed in Newtons, exerted by said item when it is slipped onto the lower or upper limb.

R is the radius of curvature at the relevant point of the lower or upper limb.

The greater the deficiency of the venous system, the more blood has difficulties for reflowing from the ankle back towards the heart, and the higher is the pressure to be exerted at the ankle.

As an example in the French system, the compression levels may be distributed in this way:

| | |
|---|---|
| Class I: 13 to 20 hPa | Class II: 20.1 to 27 hPa |
| Class III: 27.1 hPa to 48 hPa | Class IV: more than 48 hPa |

The compression items, notably of a high class, are difficult to slip on by the patient, notably when the latter suffers from reduced mobility.

Usually, medical compression stockings (or with a compressive effect) consist of two yarns, i.e. a weft yarn and a so-called knitting yarn. A weft yarn is an elastic yarn for which the travel is quasi-linear in the direction of the rows of stitches of compression items. The weft yarn gives the possibility of assigning the compressive effect to the compression item. The knitting yarn, also called background yarn gives the knitted compression item its dimensions as well as its comfort and esthetical properties.

In the state of the art, medical compression items are knitted on single-cylinder circular knitting machines with a transfer plate or on rectilinear machines with double needle bed, productivity being better with circular machines.

In the case of the production of a medical compression item on a single-cylinder knitting machine, the used knitting is generally of the plain stocking stitch type. In order that the weft yarn be secured to the knitted compression item, it produces tuck stitches or even sometimes loop stitches, on the knitting yarn, the weft yarn is then blocked in the feet of all or part of the knitted stitches with the knitting yarn.

When it is desired to assign a "rib" effect to the compression item, the knitting yarn or background yarn produces rows of knit stitches while the weft yarn produces tuck stitches with different ratios. The wider the ribbing, the more the float produced by the weft yarn on the back of the knit is also wide. These weft yarn floats being apparent on the back face of the knitted item form clinging areas and friction areas for the skin upon slipping on the item onto the leg thereby complicating its proper positioning.

The tuck stitch areas of the weft yarn form areas blocking the weft yarn in the transverse direction of the knitted tubular item limiting its elasticity, and make it even more difficult to put it into place and remove the compression item.

Thus there exists a need for a compression item not having any clinging and/or frictional areas with the skin and very easy to slip on while improving the comfort of said item.

Further, the finishing of the border or upper peripheral area downstream from the leg part of the compression item from which the foot is inserted into the item, involves blocking the knitting and weft yarns in order to avoid any fraying.

A first finishing technique quite simply consists of ending said upper peripheral area with sewing. This technique has the drawback that the back is not very esthetical and that it limits the elasticity of said area comparatively with the remainder of the compression item, which generates a border which does not remain in position on the leg, tends to slip and roll, and may prove to be uncomfortable.

A second technique consists of producing a welt by knitting at said upper peripheral area, said welt has a knitting weave close to the one of the remainder of the compression item but it is obtained by transferring stitches between the plate and the cylinder, more specifically between the transfer plates and the needles, thereby forming a double thickness. The thereby formed welt exerts greater pressure on the leg than the one exerted by the leg part. The welt may even, in certain cases, exert a tourniquet effect. This welt formed with double thickness is also warmer than the remainder of said compression item. Finally, according to the morphology of the patient, it tends to slip.

Therefore there exists a need for a tubular compression item exerting a compressive force on the ankle as far as the calf which is perfectly gradual and the border or peripheral area of which does not slip or roll on the leg and is not thicker, i.e. having a basis weight ($g/m^2$) which is not larger than that of the remainder of the compression item.

OBJECT AND SUMMARY OF THE INVENTION

The present invention overcomes all or part of the aforementioned problems in that it relates according to a first aspect to a tubular compression item, of a compression sock, compression stocking or compression knee-length stocking, or compression panty hose-type having at least one knitted leg part, one knitted foot tip, one knitted heel, one knitted foot and one knitted ribbed edge in the extension of the leg part delimiting an opening for introducing the foot into said item, said knitted leg part having a height extending from the knitted foot part up to the knitted ribbed edge. The knitted leg part, the knitted foot and the knitted ribbed edge of the tubular compression item each comprise at least one knitting yarn and the knitted leg part comprises rows of n*p ribbed stitches and has inner and outer faces, the knitted foot comprises rows of n'*p' ribbed stitches and has inner and outer faces, and the knitted ribbed edge comprises rows of n"*p" ribbed stitches and has inner and outer faces, (m), (n), (n'), (n"), (p), (p') and (p") being integers greater than or equal to 1. Each of the knitted leg part, the knitted foot and the knitted ribbed edge of the tubular compression item comprise rows of stitches and columns of stitches and an elastic weft yarn is inserted between: the knitted stitches on the outer face and the knitted stitches on the inner face of the knitted leg part in every row to every five rows of stitches over all the knitted leg part's height. The knitted stitches on the outer face and the knitted stitches on the inner face of the knitted foot in every row to every five rows of stitches in the foot, and the knitted stitches on the outer face and the knitted stitches on the inner face of the knitted ribbed edge in every two rows to every five rows of stitches in the ribbed edge, and the elastic weft yarn is inserted, on at least 90% of the columns of stitches in the knitted leg part, the knitted foot and the knitted ribbed edge, for one row of stitches, without forming any tuck stitch, or loop stitch. An elastic weft yarn density in the knitted ribbed edge being less than or equal to a weft yarn density in the knitted leg part, the elastic weft yarn density being the insertion of the elastic weft yarn every b rows of stitches, b being an integer greater than or equal to 1. The elastic weft yarn is disposed and maintained between two consecutive rows of stitches in the knitted leg part, and the knitted foot tip and the knitted heel each comprise at least one knitting yarn. The elastic weft yarn has a count at least three times greater than the count of the knitting yarn, and the knitted leg part, the knitted foot part, and the knitted ribbed edge are of the same knitting pattern and comprise only ribbed stitches. The knitted leg part comprises a circular area A and a circular area B, wherein the circular area A and the circular area B are consecutive and distinct, and wherein a circumference of the circular area A is less than a circumference of the circular area B, and the knitted leg part has a frusto-conical shape.

Advantageously, a double cylinder knitting machine gives the possibility of laying the weft yarn between two rows of consecutive stitches without blocking it by having it pass through the feet of the stitches so that the weft yarn is found between the knitted stitches on the location forming the outer face of the item and the knitted stitches on the back forming the inner face of the compression item. In the leg part and foot portions knitted with a knitting yarn along ribbed stitches and an elastic weft yarn, the weft yarn thus forms a somewhat intermediate layer positioned between the outer and inner faces and will not come directly into contact with the skin thereby avoiding the formation of clinging and/or frictional areas with the skin. Slipping on the item is thereby facilitated and the comfort of the contact of said item is improved.

Further, when the weft yarn is simply laid between two rows of consecutive stitches, it is not blocked in the feet of plain and/or purl stitches so that the elasticity of the thereby knitted areas is greater for a same compressive effect. This arrangement further improves comfort, facilitates slipping on and limits slip on the leg, of said item.

Finally, the ribs according to the invention are "real" ribbed stitches. Indeed, in the state of the art when a single cylinder knitting machine is used, the ribs are formed by bringing closer the weft yarn feeding areas, and therefore somewhat by puckering up the knitted areas positioned between these feed areas.

In the present text, the terms of "ribbed stitches" or "rib stitches" are used equally. The knitted foot tip and the knitted heel may not comprise an elastic weft yarn.

The knitted ribbed edge may have a height (h) at least of 1 mm.

The knitted ribbed edge may have a height (h) at least of 20 mm.

The knitted ribbed edge may have a height (h) at least of 50 mm.

The elastic yarn may be disposed and maintained between two consecutive rows of stitches in the knitted foot and in the knitted ribbed edge.

The elastic weft yarn may form one or several tuck stitches in one or more of the knitted leg part, the knitted foot, and the knitted ribbed edge.

The elastic weft yarn may be inserted every row to every two rows of stitches over all the knitted leg part's height, and in the knitted foot.

The elastic weft yarn may consist of an elastane yarn covered with one or more yarns.

The elastic weft yarn may have a count comprised between 150 dtex and 2,000 dtex.

The elastic weft yarn may have a count comprised between 300 dtex and 1,500 dtex.

The elastic weft yarn may have a count at least five times greater than that of the knitting yarn.

The knitting yarn may have a count comprised between 15 dtex and 500 dtex.

The knitting yarn may have a count comprised between 20 dtex and 300 dtex.

The knitting yarn may consist of a elastane yarn covered with one yarn or at least two yarns.

The knitting yarn may have a count comprised between 150 dtex and 2000 dtex.

The knitted foot tip and the knitted heel may each include an elastic weft yarn.

The knitted foot tip and the knitted heel may each include one or several rows of plain and/or purl jersey stitches knitted with the knitted yarn.

The elastic weft yarn may have an elongation at break greater than or equal to 100%.

The elastic weft yarn may form an intermediate layer when positioned between the knitted stitches on the outer face and the knitted stitches on the inner face of the knitted leg part, of the knitted foot, and of the ribbed edge.

SHORT DESCRIPTION OF THE DRAWINGS

The present invention will be better understood upon reading an exemplary embodiment mentioned as non-limiting and illustrated by the following figures wherein.

DETAILED DESCRIPTION OF THE INVENTION

Figure 1:
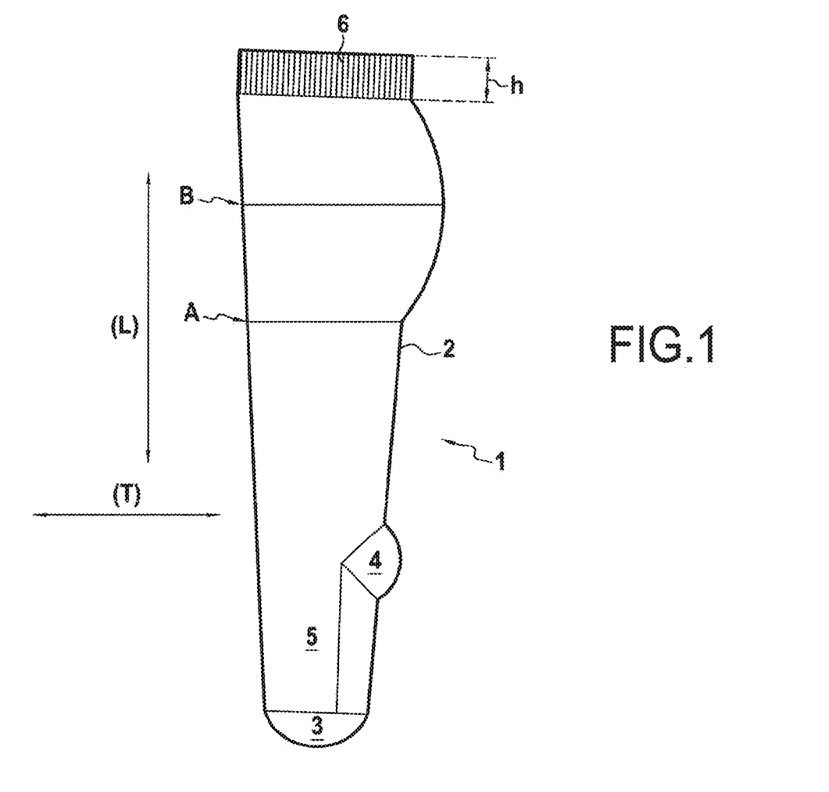
FIG. 1 schematically illustrates a tubular compression item according to the invention, in particular a compression sock.

The tubular compression item 1 illustrated in FIG. 1 is a sock comprising a leg part 2, a foot tip 3, a heel 4, a foot 5 and a ribbed edge 6 in the extension of the leg part 2.

The whole of the item 1 is knitted on a double cylinder knitting machine, i.e. comprising upper and lower superposed cylinders each working with a determined number of needles (m).

The tubular item 1 comprises a longitudinal direction (L) and a transverse direction (T) corresponding to the direction of the columns of stitches and to the direction of rows of stitches respectively.

Figure 2:
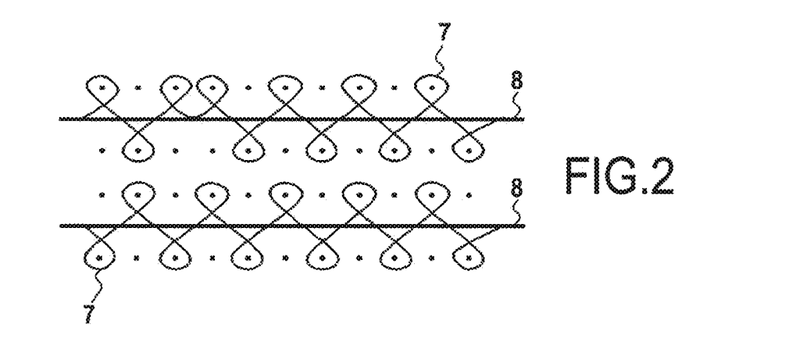
FIG. 2 schematically illustrates the knitting weave of the leg part and of the foot of the compressive sock illustrated in FIG. 1.

The leg part 2, the foot 5 and the ribbed edge 6 comprise several rows of ribbed stitches respectively (n)*(p), (n')*(p') and (n")*(p") knitted with a knitting yarn 7 illustrated in FIG. 2, between which are inserted elastic weft yarn 8 every 1/1 to 1/5 rows of stitches. In this specific example, the elastic weft yarn 8 is inserted every 1/1 to 1/2 rows of ribbed stitches (n)*(p) and (n')*(p'), preferably between all the rows of ribbed stitches, in the leg part 2 and in the foot 5 without forming any tuck stitch or loop stitch on at least 50% by number of the number of worked needles (m), in this specific example without forming any tuck stitch or loop stitch on all the worked needles (m). The weft yarn density 8 is less significant in the ribbed edge 6 since the weft yarn 8 is preferably inserted every 1/2 or more rows of ribbed stitches (n")*(p").

The elastic weft yarn 8 may be inserted between two rows of ribbed stitches by forming a few tuck stitches according to the desired effect, preferably the weft yarn 8 does not form any tuck stitch and is simply laid between the needles of the upper cylinder and the needles of the lower cylinder.

Preferably, the ribbed edge 6, the leg part 2 and the foot 5 only comprise ribbed stitches, in particular the leg part 2 and the foot 5 comprise ribbed rows 2/4 alternating with rows of dimension 1/1, the knitting weaves are thus illustrated in FIG. 2.

Figure 3:
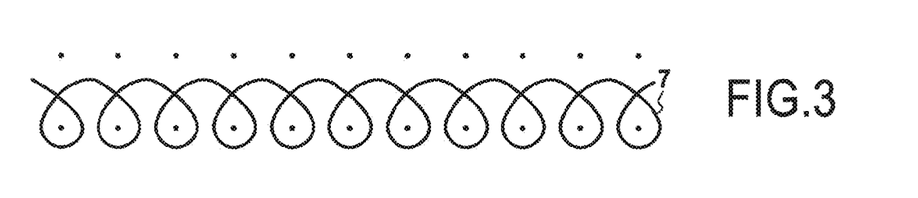
FIG. 3 schematically illustrates the knitting weave of the heel and of the foot tip of the compressive sock illustrated in FIG. 1.

Preferably, the heel 4 and the foot tip 3 do not comprise an elastic weft yarn inserted in the weft and are knitted from the knitting yarn 8 according to jersey stitches, preferably knit jersey stitches, the knitting weave of which is illustrated in FIG. 3. The black dots illustrate in FIGS. 2 and 3 the needles of the upper and lower cylinders.

The leg part 2 comprises two consecutive circular areas A and B, the height of which is of the order of 5 mm.

As a specific example, the compression sock 1 according to the invention is knitted in its whole from the knitting yarn 7 comprising a yarn with an elastic core, in particular an elastane yarn of 44 dtex, covered with a first covering yarn, notably a yarn in polyamide 6-6 with two ends of 78 dtex each, and a second covering yarn, notably in cotton at one end of 120 Nm; and a weft yarn 8 (only for the leg part, the foot and the ribbed edge), comprising a yarn with an elastic core, in particular an elastane yarn of 330 dtex, covered with a first covering yarn, notably a polyamide yarn at an end of 22 dtex, and a second covering yarn, notably in cotton at an end of 160 Nm.

With the purpose of testing the elasticity performances of the compression sock according to the invention, a sock from the state of the art is knitted on a single cylinder knitting machine (i.e. cylinder-transfer plate, also designated under the term of «cylinder-dial») so as to substantially have the same dimensions, i.e. the same size, for the same medical compression class, i.e. class II as well as a welt formed with a double thickness. The compression sock of the state of the art is thus knitted from a knitting yarn comprising a yarn with an elastic core, in particular an elastane yarn of 22 dtex, covered with a first covering yarn, notably at an end of 78 dtex in polyamide 6-6 and with a second covering yarn, notably in cotton at an end of 160 Nm; and a weft yarn comprising a yarn with an elastic core, notably an elastane yarn of 330 dtex, covered with a first covering yarn, notably in polyamide 6-6 at an end of 22 dtex and of a second covering yarn, notably in cotton at an end of 160 Nm for the welt, the leg part and the foot. For the foot tip and the heel, the sock of the state of the art does not comprise any elastic weft yarn but a knitting yarn comprising a yarn with an elastic core, in particular an elastane yarn of 78 dtex, covered with a first covering yarn, notably a yarn in polyamide 6-6 at an end of 78 dtex, and with a second covering yarn, notably a cotton yarn at an end of 160 Nm. In order to produce a ribbed leg part and foot, the knitting yarn is knitted with a stocking stitch while the weft yarn produces tuck stitches with ratios of 1/2, 1/3 and 2/3.

Figure 4:
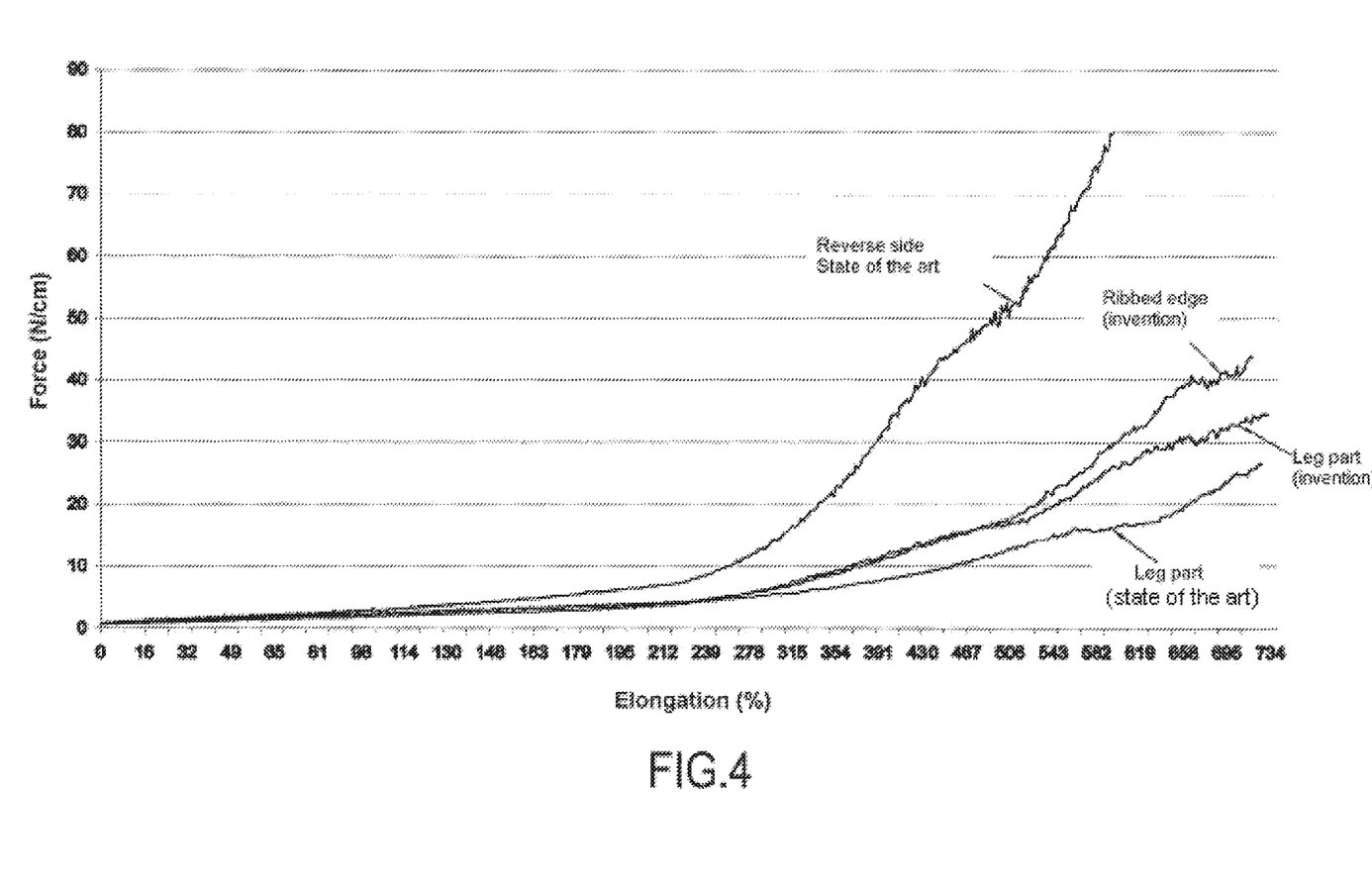
FIG. 4 illustrates a graph comparing the forces and elongations at break obtained for the leg part and for the ribbed edge of the item described in FIG. 1 with the forces and elongations at break of the leg part and of the welt of a compressive item of the state of the art, said compressive items being classified as belonging to the medical compression class II.
Figure 5A:
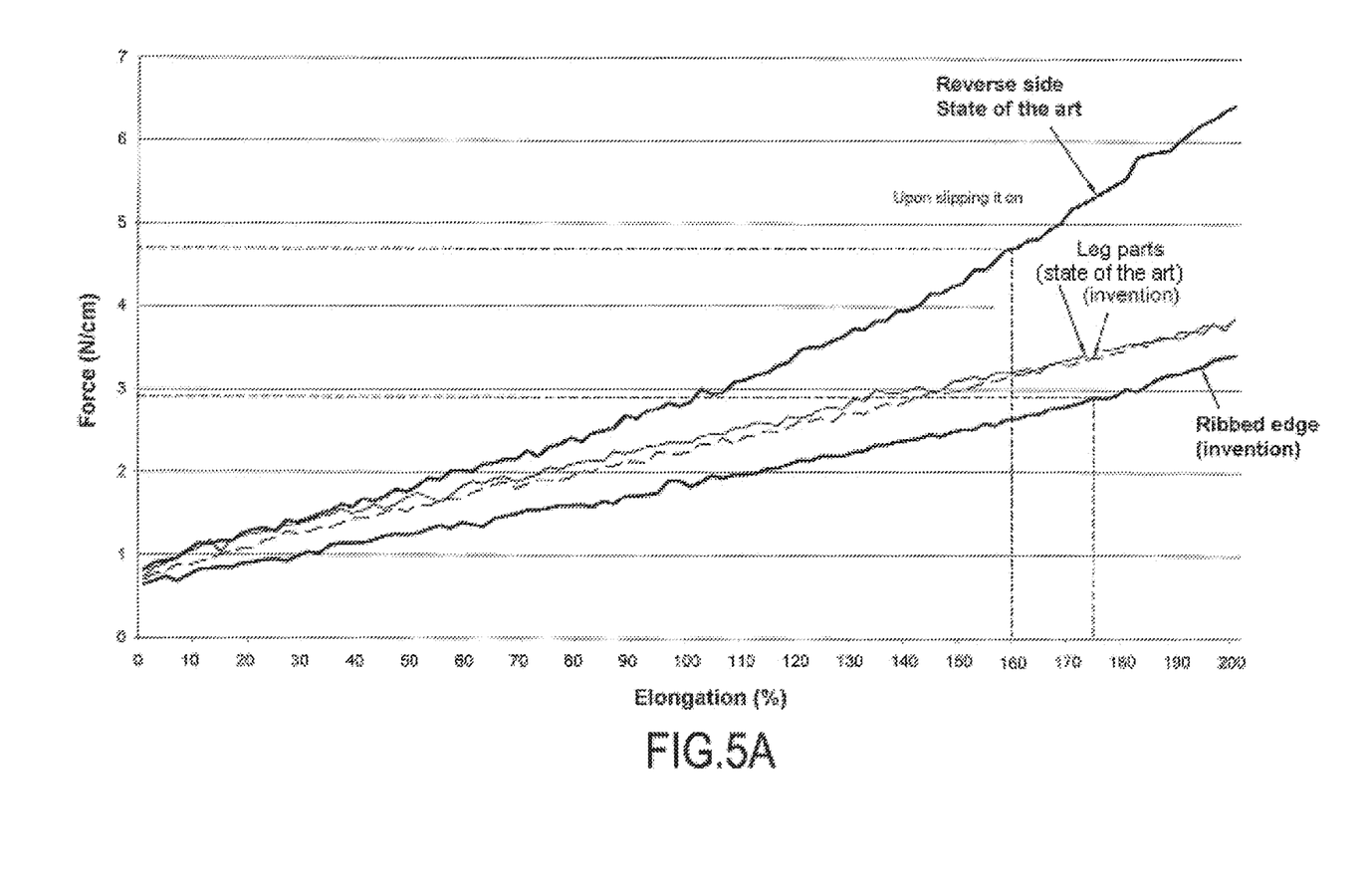
FIG. 5A illustrates curves comparing the forces to be applied for slipping on a compressive item according to the invention and a compressive item of the state of the art.
Figure 5B:
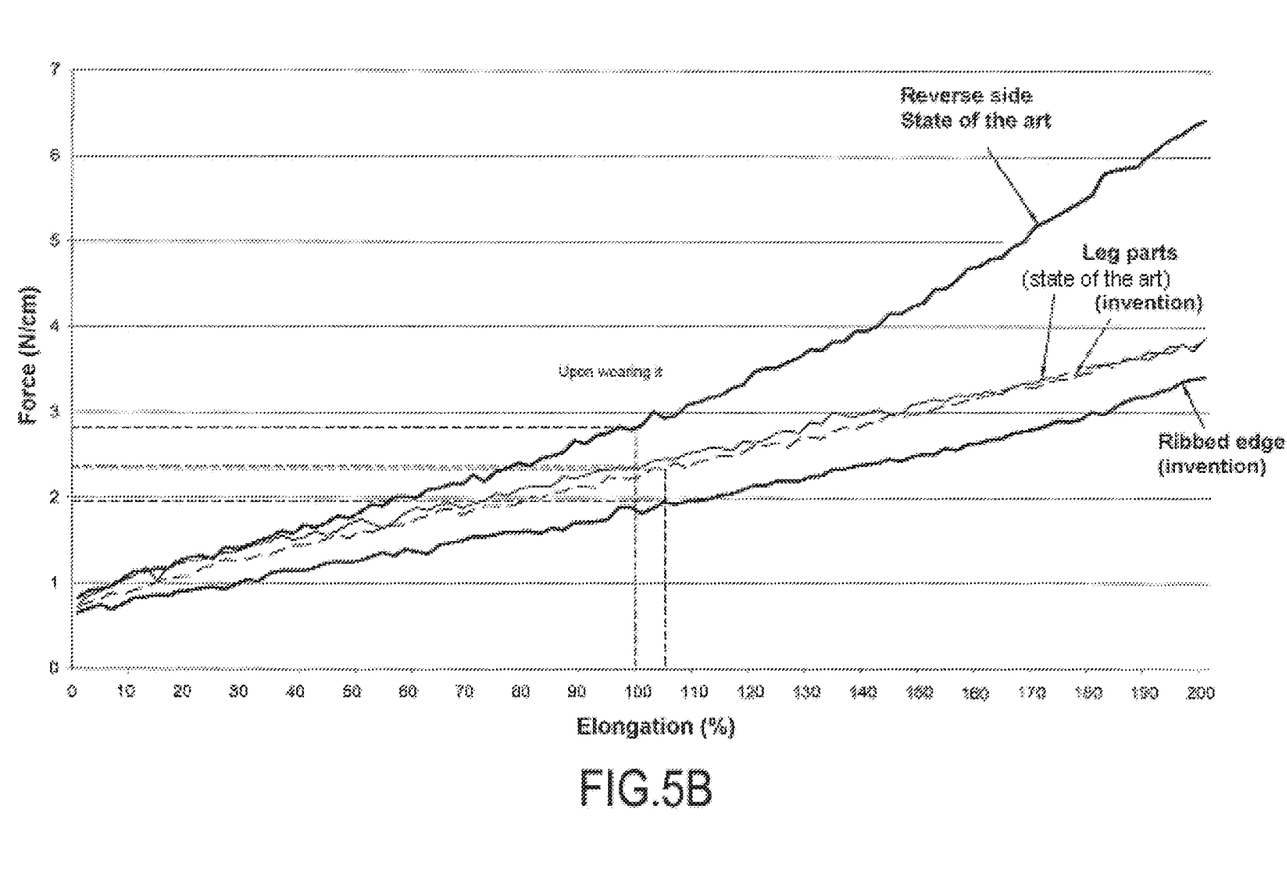
FIG. 5B illustrates curves comparing the forces and elongations obtained when the compressive item according to the invention and a compressive item of the state of the art are worn.

The curves of forces and elongations illustrated in FIGS. 4, 5A and 5B resume the measurement values conducted according to the NF 14-704-1 standard of June 2005. The compression forces at the ankle exerted by the compression sock according to the invention and by the sock of the state of the art are equivalent and measured according to the NF G30-102 B standard as of October 1986. The flat width at rest of the sock 1 according to the invention measured at the beginning of the ribbed edge on the leg part is 95 mm; it is 90 mm as regards the width at the beginning of the reverse side on the leg part of the compression sock of the state of the art. The compression socks to be tested are positioned on a Hohenstein leg so that they are in compliance with their placement upon wearing. On each of the socks, the height of the ribbed edge (h1) and the height of the welt (h2) are measured and transferred under the latter on the leg part. Annular ribbed edge and welt strips as well as leg part strips, respectively with a height (h1) and (h2) are cut out in each compression sock. These annular strips are open so as to form rectangular test specimens, the widths of which correspond to the wearer heights (h1) and (h2). Each of these specimens are placed on a force gauge and evaluated according to the aforementioned NF 14-704-1 standard. The gap between the jaws of the force gauge was adjusted to 50 mm.

The measurement of the forces and elongations is carried out in compliance with the wearing behavior of the compression socks; thus the welt is tested in a double thickness while the ribbed edge and the leg part strips are tested in a single thickness.

It is thus noted that the ribbed edge 6 has a greater elongation at break (about 716%) than that of the welt of the state of the art (about 596%). Moreover, the elastic behaviors of the leg part of the sock of the state of the art and of its welt diverge; the tourniquet effect of the criticized welt is thus again found. On the contrary, the elastic behaviors of the ribbed edge and of the leg part of the sock according to the invention are very close (respectively 716% and 728% of elongations at break) thus allowing very homogenous gradual decrease in the exerted compression to be obtained.

It is also noted that the force at breakage of the leg part of the compression sock according to the invention (34.5 N/cm) is greater by 29% than the force at breakage of the leg part of the sock of the state of the art (26.7 N/cm). A non-exhaustive explanation of this effect is that the elastic weft yarns do not form any tuck stitch or loop stitch, in the compression sock according to the invention, or optionally very few tuck stitches, while in the sock of the state of the art, the weft yarns form tuck stitches at very regular intervals, said tuck stitches forming anchoring and therefore blocking points of the stitched structure.

Table 1 below resumes values extracted from FIGS. 5A and 5B illustrating the behavior of the compression socks according to the invention and of the state of the art according to the ranges of use, i.e. upon wearing under an elongation ranging from 100% to 105% and upon slipping them on under an elongation ranging from 160% to 175%.

It is thus noted that two different elongations are transferred onto FIGS. 5A and 5B since the width of the tested areas at rest are different for the compression item according to the invention (90 mm) and the compression item of the state of the art (95 mm). These differences in lengths are due to the knitting machines used: either with one cylinder or two cylinders.

TABLE 1

|  |  | Sock of the state of the art | Sock according to the invention |
| --- | --- | --- | --- |
| At rest | Ribbed edge or welt width (mm) | 95 | 90 |
|  | Circumference (mm) | 190 | 180 |
| Upon wearing | Elongation (%) | 100 | 105 |
|  | Ribbed edge or welt force (N/cm) | 2.88 | 2.03 |
|  | Leg part force (N/cm) | 2.34 | 2.35 |
| Upon slipping them on | Elongation (%) | 160 | 175 |
|  | Ribbed edge or welt force (N/cm) | 4.72 | 2.86 |
|  | Leg part force (N/cm) | 3.18 | 3.38 |

The required force (N/cm) for slipping on the ribbed edge is less than 65% of that required for slipping on the welt of the compression sock of the state of the art. When the compression sock according to the invention is worn, the ribbed edge exerts a 16% less force (N/cm) than that exerted by the leg part, the gradual decrease of the exerted compression is thus perfectly observed. On the contrary, for the compression sock of the state of the art, the welt exerts a force (N/cm) 23% greater than that exerted by the leg part, the gradual decrease of the exerted compression is thus not perfectly ensured. Of course, because of the morphology of the leg, the radius of curvature being greater at the portion of the leg part covering the leg than that of the portion of the leg part covering the ankle, a global gradual decrease of the exerted compression is obtained all the same between the ankle and the leg. However, this gradual decrease is not perfectly regular and therefore homogenous between the ankle and the leg.

The compression sock according to the invention gives the possibility of improving comfort by preventing that the weft yarn forms significant floats on the reverse face of said sock, the latter arrangement combined with a ribbed edge also facilitates the slipping on of said sock 1.

Figure 6:
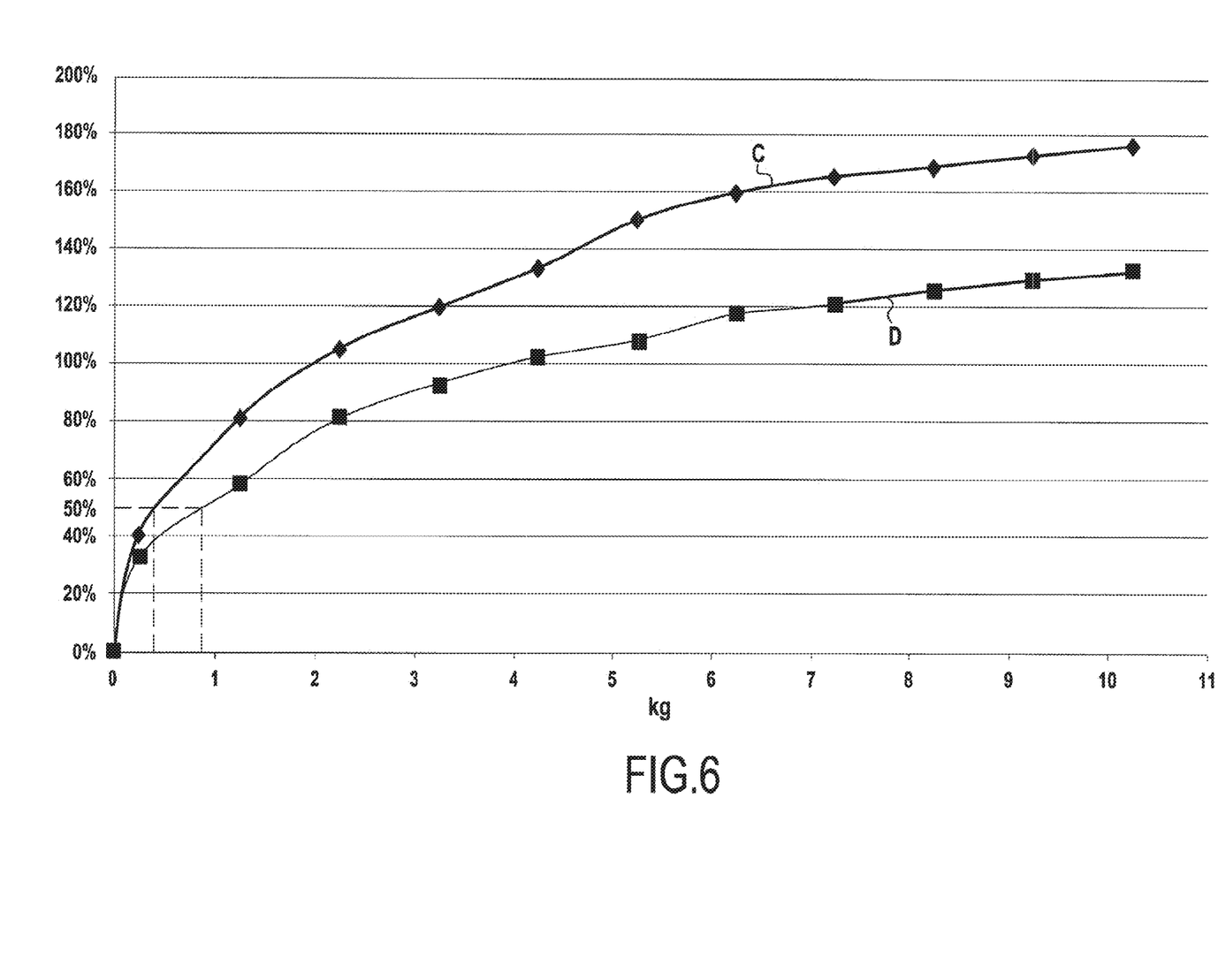
FIG. 6 illustrates two curves comparing the elongations obtained under the effect of a determined weight for a compressive item according to the invention (curve (C)), and a compressive item of the state of the art (curve (D))

FIG. 6 illustrates two curves (C, D) obtained by the extensibility test method described hereafter conducted on the leg parts of the compression sock 1 according to the invention and on the compression sock of the state of the art tested with reference to FIGS. 4, 5A and 5B, both having a compression level of class II.

The two tested socks have the same leg part height between the heel and the beginning of the welt or of the ribbed edge, i.e. 21 cm. Both socks also have the same size, the circumference at the ankle is 27.5 cm and the circumference at the calf is 41.5 cm. The height of the socks is 44 cm.

The socks are suspended on an extension bench by means of a first clamp clamping the socks on the leg part at the beginning of the welt or of the ribbed edge. A second clamp, movable relatively to the extension bench, is secured to the socks in the lower portion of the leg parts at the demarcation of the heel. Weights are hooked up on the second clamp so as to cause extension in the vertical direction of the leg parts of said socks. The extension bench is provided with a graduation allowing measurement of the obtained elongation according to the total weight applied at the second clamp.

The mass of the second clamp is 0.250 kg and the mass of each weight is 1 kg. The measurement of the extension of the leg parts is noted for the second clamp alone, and then by gradually adding a weight of 1 kg up to a total weight of 10 kg.

It is considered that when the compression socks are worn by the user, the leg parts are stretched by at least 50% of their lengths at rest.

Thus, in FIG. 6 it is observed that for an elongation of 50%, the force (kg) to be exerted for bringing the leg part to its application size is less for the compression sock according to the invention than the one required for the compression sock of the state of the art. Now, this force (kg) is also the one which is applied to the ribbed edge or to the welt when the compression sock is placed on the leg. The force or traction exerted by the compression sock according to the invention in the transverse direction (T) is about equal to 50% of the force exerted on the compression sock of the state of the art for a same elongation (%).

Thus, the conclusion may be drawn that the compression sock obtained by the method according to the invention has a better hold on the leg than the compression sock of the state of the art. Indeed, the compression sock according to the invention will have much less tendency to slip on the leg than the compression sock of the state of the art. This technical effect is explained by the design of the compression sock according to the invention, which comprises a freely positioned weft yarn between two consecutive rows of stitches, at least on 50% by number of the number (m) of the knitted needles without forming any tuck stitch or loop stitch. Maintaining a compression sock in place when it is worn is a balance between the compression exerted transversely and the elongation exerted by the leg on the sock between the ribbed edge or welt of the sock and the ankle.

The histograms illustrated in FIGS. 7A to 7D resume measurements conducted on compression socks according to the invention and of the state of the art described above and of class II according to the measurement method described hereafter. The measurements are conducted on the ribbed edge of the sock according to the invention (single thickness) and on the welt (double thickness) of the sock of the state of the art.

The weight composition of said socks is substantially equivalent:
  47% cotton, 43% polyamide and 10% elastane for the sock according to the invention,
  50% cotton, 38% polyamide, 12% elastane for the sock of the state of the art.

The compression socks were washed so as to remove all the residues stemming from the production methods. The sock specimens were taken on a standardized leg of the Hohenstein type.

The specimens, during the measurements, were stretched by at least 50% of their length at rest, which corresponds to the behavior of compression socks when they are worn.

This test method thus has the purpose of studying the dynamics of the transfer of steam through a textile part which has been put into contact beforehand with a known amount of water, in particular 1 mg of water, which corresponds to a drop of sweat. The flow density of steam evolved by the tested specimen is measured and studied over time. The device on which the test is conducted comprises a heating support heated to a temperature corresponding to the body temperature (35° C.), a sample holder, and a measurement cell, such as a Peltier measurement cell equipped with a regulator. The support, mounted facing the specimen holder, is preferably in copper and may be covered with a latex layer so as to reproduce human skin. The specimen holder is made so as to ensure the seal of the assembly formed with the support, the specimen and the measurement cell. Thus, ambient humidity and temperature variations do not have any incidence on the measurement. The measurement cell comprises a flowmeter and a condenser allowing discharge of humidity.

The time-dependent change in the flow density of steam through the specimens comprises the following steps: putting the specimen into contact with a drop of water corresponding to the absorption phase, a phase for transferring humidity into the specimen or diffusion phases followed by evaporation and drying phases.

Figure 7A:
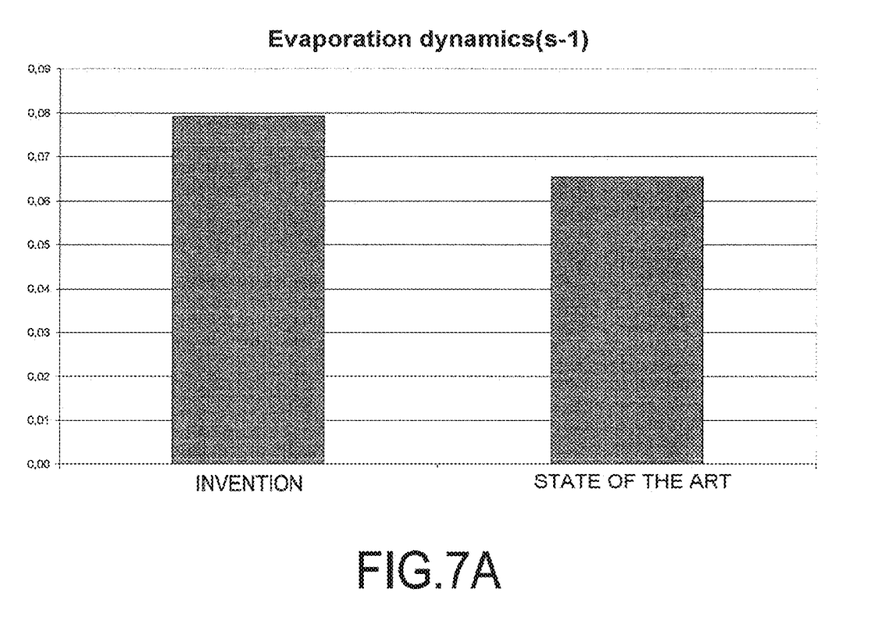
FIGS. 7A to 7D illustrate histograms comparing the humidity absorption properties (FIG. 7A), humidity removal properties (FIG. 7B), drying properties (FIG. 7C), and humidity retention properties (FIG. 7D) between compressive socks according to the invention and according to the state of the art described above with reference to FIGS. 1 to 6.
Figure 7B:
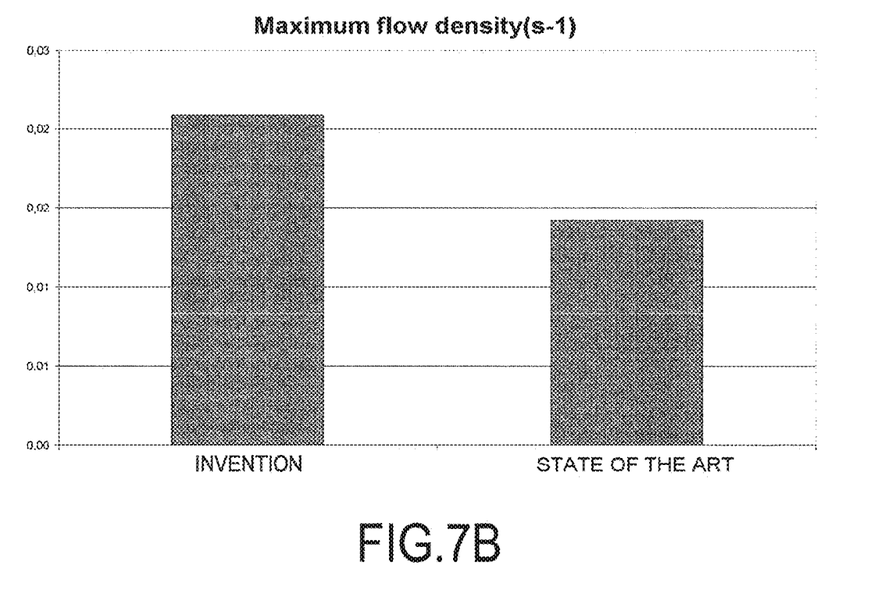
Figure 7C:
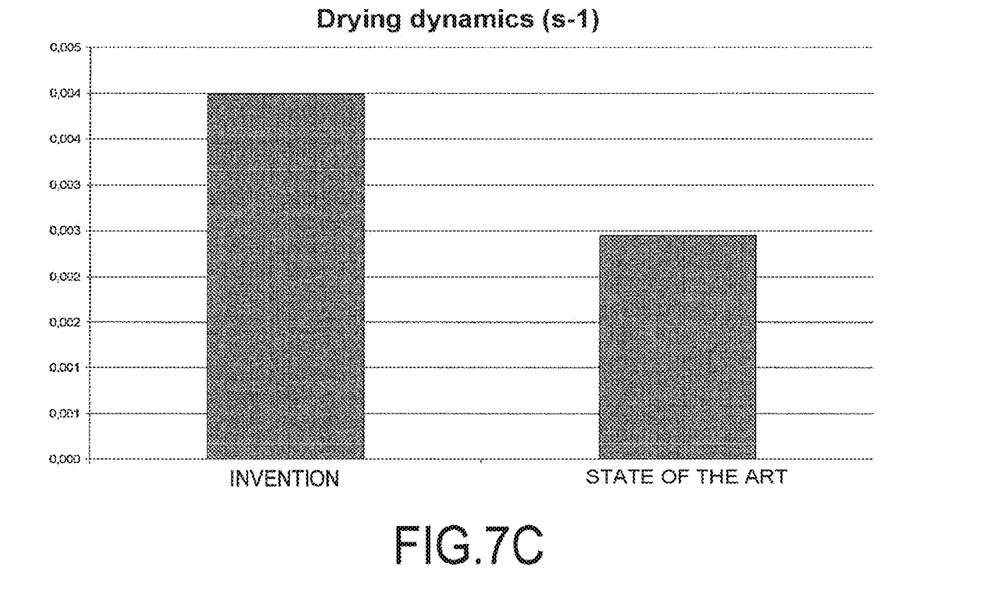
Figure 7D:
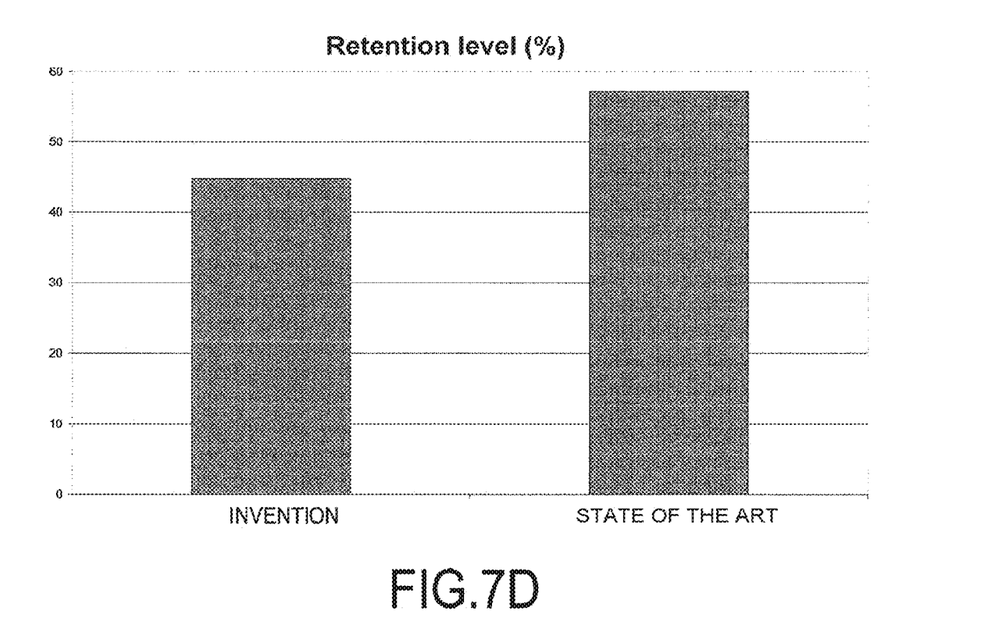
Figure 8:
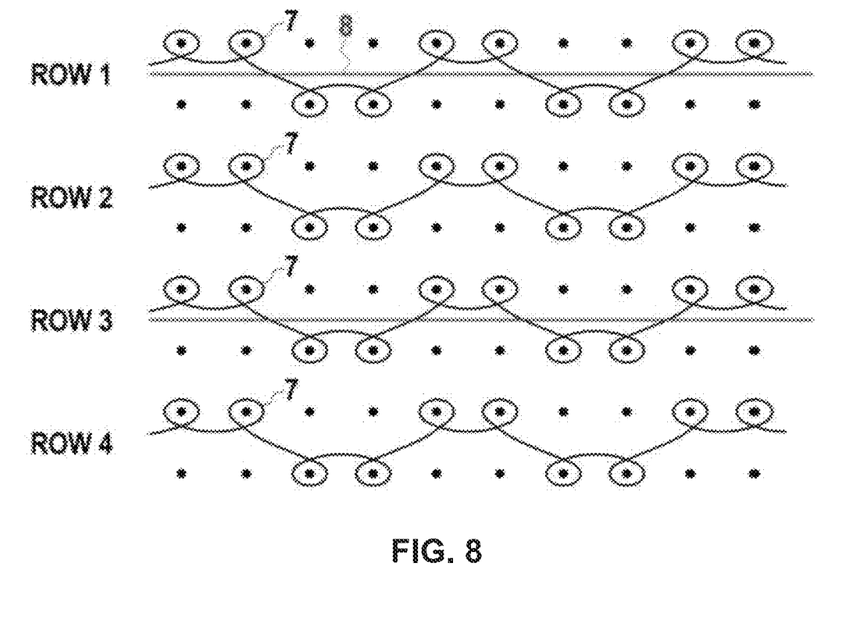
FIG. 8 schematically illustrates an example knitting weave of the leg part and of the foot of the compressive sock illustrated in FIG. 1.

FIG. 7A corresponds to the humidity absorption phase during the putting into contact of the specimens with a drop of water. FIGS. 7B and 7C respectively correspond to the capability of the specimens to discharge the humidity based on the maximum steam flow density and the drying dynamics. Finally, FIG. 7D corresponds to the retention rate of the amount of water maintained in the specimens after the test, i.e. after their drying.

Upon reading these histograms, one notices that the compression sock according to the invention is superior in all points to the compression sock of the state of the art. The ribbed edge of the compression sock according to the invention thus absorbs more rapidly humidity, discharges it and dries more rapidly than the welt of the compression sock of the state of the art. Further, the ribbed edge of the compression sock according to the invention finally retains less humidity than the welt of the sock of the state of the art once the test is completed.

As a conclusion, the sock according to the invention significantly improves the thermal comfort of the user.

What is claimed is:

1. A tubular compression item, of a compression sock, compression stocking or compression knee-length stocking, or compression panty hose-type comprising a knitted leg part, a knitted foot tip, a knitted heel, a knitted foot and a knitted ribbed edge in the extension of the leg part delimiting an opening for introducing a foot into said item, said knitted leg part having a height extending continuously from said knitted foot part up to said knitted ribbed edge and said knitted leg part comprises a first end adjacent to the knitted ribbed edge and a second end adjacent to the knitted foot, the height of the knitted leg part being the distance between the first and second ends,
  wherein the knitted leg part, the knitted foot and the knitted ribbed edge of the tubular compression item each comprise at least one knitting yarn,
  wherein the knitted leg part comprises rows of n*p ribbed stitches and has inner and outer faces, the knitted foot comprises rows of n'*p' ribbed stitches and has inner and outer faces, and the knitted ribbed edge comprises rows of n"*p" ribbed stitches and has inner and outer faces, with n, n', n", p, p' and p" being integers greater than or equal to one,
  wherein each of the knitted leg part, the knitted foot and the knitted ribbed edge of the tubular compression item comprise rows of stitches and columns of stitches,
  and wherein an elastic weft yarn is inserted between: the knitted stitches of the outer face and the knitted stitches of the inner face of the knitted leg part in every row to every five rows of stitches over the entire height of the knitted leg part, the knitted stitches of the outer face and the knitted stitches of the inner face of the knitted foot in every row to every five rows of stitches in the foot; and the knitted stitches of the outer face and the knitted stitches of the inner face of the knitted ribbed edge in every two rows to every five rows of stitches in the ribbed edge,
  and wherein the elastic weft yarn is inserted, on at least 90% of the columns of stitches in the knitted leg part, the knitted foot and the knitted ribbed edge, for one row of stitches, without forming any tuck stitch or loop stitch,
  and wherein an elastic weft yarn density in the knitted ribbed edge is less than or equal to a weft yarn density in the knitted leg part, the elastic weft yarn density being the insertion of the elastic weft yarn every b rows of stitches, with b being an integer greater than or equal to one,
  and wherein the elastic weft yarn is disposed and maintained between two consecutive rows of stitches in the knitted leg part, and
  wherein the knitted foot tip and the knitted heel each comprise at least one knitting yarn,
  and wherein the elastic weft yarn has a count at least three times greater than the count of the knitting yarn, and wherein the knitted leg part, the knitted foot part, and the knitted ribbed edge are of the same knitting pattern and comprise only ribbed stitches, and wherein the knitted leg part comprises a circular area A and a circular area B, wherein the circular area A and the circular area B are consecutive and distinct, and wherein a circumference of the circular area A is less than a circumference of the circular area B, and said entire knitted leg part, considered from its first end to its second end, has a frusto-conical shape.

2. The tubular compression item according to claim 1, wherein the knitted foot tip and the knitted heel do not comprise the elastic weft yarn.

3. The tubular compression item according to claim 1, wherein the knitted ribbed edge has a height of at least of 1 mm.

4. The tubular compression item according to claim 1, wherein the knitted ribbed edge has a height of at least of 20 mm.

5. The tubular compression item according to claim 1, wherein the knitted ribbed edge has a height of at least of 50 mm.

6. The tubular compression item according to claim 1, wherein the elastic weft yarn is disposed and maintained between two consecutive rows of stitches in the knitted foot and between two consecutive rows of stitches in the knitted ribbed edge.

7. The tubular compression item according to claim 1, wherein the elastic weft yarn forms one or several tuck stitches in one or more of the knitted leg part, the knitted foot, and the knitted ribbed edge.

8. The tubular compression item according to claim 1, wherein the elastic weft yarn is inserted every row to every two rows of stitches over the entire height of the knitted leg part, and in the knitted foot.

9. The tubular compression item according to claim 1, wherein the elastic weft yarn consists of an elastane yarn covered with one or more yarns.

10. The tubular compression item according to claim 1, wherein the elastic weft yarn has a count comprised between 150 dtex and 2,000 dtex.

11. The tubular compression item according to claim 1, wherein the elastic weft yarn has a count comprised between 300 dtex and 1,500 dtex.

12. The tubular compression item according to claim 1, wherein the elastic weft yarn has a count at least five times greater than that of the knitting yarn.

13. The tubular compression item according to claim 1, wherein the knitting yarn has a count comprised between 15 dtex and 500 dtex.

14. The tubular compression item according to claim 1, wherein the knitting yarn has a count comprised between 20 dtex and 300 dtex.

15. The tubular compression item according to claim 1, wherein the knitting yarn consists of an elastane yarn covered with one yarn or at least two yarns.

16. The tubular compression item according to claim 15, wherein the knitting yarn has a count comprised between 150 dtex and 2000 dtex.

17. The tubular compression item according to claim 1, wherein the knitted foot tip and the knitted heel each comprises an elastic weft yarn.

18. The tubular compression item according to claim 1, wherein the knitted foot tip and the knitted heel each comprises one or several rows of plain and/or purl jersey stitches knitted with the knitted yarn.

19. The tubular compression item according to claim 1, wherein the elastic weft yarn has an elongation at break greater than or equal to 100%.

20. The tubular compression item according to claim 1, wherein the elastic weft yarn forms an intermediate layer when positioned between the knitted stitches on the outer face and the knitted stitches on the inner face of the knitted leg part, of the knitted foot, and of the ribbed edge.

* * * * *